United States Patent
Boyd et al.

(10) Patent No.: US 7,968,578 B2
(45) Date of Patent: Jun. 28, 2011

(54) INDOLE AMIDE DERIVATIVES AS EP4 RECEPTOR ANTAGONISTS

(75) Inventors: Michael Boyd, Montreal (CA); John Colucci, Kirkland (CA); Zhaoyin Wang, Kirkland (CA)

(73) Assignee: Merck Frosst Canada Ltd., Quebec (CA)

( * ) Notice: Subject to any disclaimer, the term of this patent is extended or adjusted under 35 U.S.C. 154(b) by 92 days.

(21) Appl. No.: 12/225,544

(22) PCT Filed: Apr. 23, 2007

(86) PCT No.: PCT/CA2007/000689
§ 371 (c)(1),
(2), (4) Date: Sep. 23, 2008

(87) PCT Pub. No.: WO2007/121578
PCT Pub. Date: Nov. 1, 2007

(65) Prior Publication Data
US 2009/0253756 A1    Oct. 8, 2009

Related U.S. Application Data

(60) Provisional application No. 60/794,557, filed on Apr. 24, 2006.

(51) Int. Cl.
| | |
|---|---|
| A61K 31/4035 | (2006.01) |
| A61K 31/404 | (2006.01) |
| A61K 31/416 | (2006.01) |
| A61K 31/4184 | (2006.01) |
| A61K 31/4192 | (2006.01) |
| A61K 31/42 | (2006.01) |
| A61K 31/425 | (2006.01) |
| C07D 275/04 | (2006.01) |
| C07D 261/20 | (2006.01) |
| C07D 249/18 | (2006.01) |
| C07D 235/06 | (2006.01) |
| C07D 231/56 | (2006.01) |
| C07D 209/10 | (2006.01) |

(52) U.S. Cl. ........ 514/373; 514/379; 514/394; 514/406; 514/415; 514/416; 548/207; 548/241; 548/261; 548/304.4; 548/362.5; 548/494

(58) Field of Classification Search .................. 548/207, 548/241, 261, 304.4, 362.5, 494
See application file for complete search history.

(56) References Cited

U.S. PATENT DOCUMENTS

| | | | |
|---|---|---|---|
| 4,221,815 A | 9/1980 | Weyer et al. | |
| 2005/0065188 A1 | 3/2005 | Nakao et al. | |
| 2006/0281750 A1* | 12/2006 | Li et al. | 514/248 |
| 2007/0123561 A1* | 5/2007 | Lee et al. | 514/303 |

FOREIGN PATENT DOCUMENTS

EP    0 166 591 A2    1/1986

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jun. 9, 2007]. Retrieved from the internet, URL; http://en.wikipedia.orglwikilCancer.*

* cited by examiner

*Primary Examiner* — Shawquia Young
(74) *Attorney, Agent, or Firm* — Valerie J. Camara; Maria V. Marucci

(57) ABSTRACT

The invention is directed to indole amide derivatives as EP4 receptor antagonists useful for the treatment of EP4 mediated diseases or conditions, such as acute and chronic pain, osteoarthritis, rheumatoid arthritis and cancer. Pharmaceutical compositions and methods of use are also included.

14 Claims, No Drawings

INDOLE AMIDE DERIVATIVES AS EP4 RECEPTOR ANTAGONISTS

CROSS REFERENCE TO RELATED APPLICATIONS

This application is a U.S. National Phase application under 35 U.S.C. §371 of PCT Application No. PCT/CA2007/000689, filed 23 Apr. 2007 which claims priority under 35 U.S.C. §119(e) from U.S. Provisional Application Ser. No. 60/794,557, filed 24 Apr. 2006.

BACKGROUND OF THE INVENTION

This invention relates to compounds and methods for treating prostaglandin E mediated diseases, and certain pharmaceutical compositions thereof. More particularly, the compounds of the invention are structurally different from NSAIDs and opiates, and are antagonists of the pain and inflammatory effects of E-type prostaglandins.

Three review articles describe the characterization and therapeutic relevance of the prostanoid receptors as well as the most commonly used selective agonists and antagonists: *Eicosanoids: From Biotechnology to Therapeutic Applications*, Folco, Samuelsson, Maclouf, and Velo eds, Plenum Press, New York, 1996, chap. 14, 137-154; Journal of Lipid Mediators and Cell Signalling, 1996, 14, 83-87; and Prostaglandins and Other Lipid Mediators, 2002, 69, 557-573.

Thus, selective prostaglandin ligands, agonists or antagonists, depending on which prostaglandin E receptor subtype is being considered, have anti-inflammatory, antipyretic and analgesic properties similar to a conventional non-steroidal anti-inflammatory drug, and in addition, have effects on vascular homeostasis, reproduction, gastrointestinal functions and bone metabolism. These compounds may have a diminished ability to induce some of the mechanism-based side effects of NSAIDs which are indiscriminate cyclooxygenase inhibitors. In particular, the compounds are believed to have a reduced potential for gastrointestinal toxicity, a reduced potential for renal side effects, a reduced effect on bleeding times and a lessened ability to induce asthma attacks in aspirin-sensitive asthmatic subjects.

In The Journal of Clinical Investigation (2002, 110, 651-658), studies suggest that chronic inflammation induced by collagen antibody injection in mice is mediated primarily through the EP4 subtype of $PGE_2$ receptors. Patent application publications WO 96/06822 (Mar. 7, 1996), WO 96/11902 (Apr. 25, 1996) and EP 752421-A1 (Jan. 8, 1997) disclose compounds as being useful in the treatment of prostaglandin mediated diseases.

The present invention is directed to novel compounds that are antagonists of the EP4 subtype of $PGE_2$ receptors. The compounds would therefore be useful for the treatment of diseases or conditions mediated by the EP4 receptor, such as acute and chronic pain, osteoarthritis, rheumatoid arthritis and cancer

SUMMARY OF THE INVENTION

The invention is directed to indole amide derivatives as EP4 receptor antagonists useful for the treatment of EP4 mediated diseases or conditions, such as acute and chronic pain, osteoarthritis, rheumatoid arthritis and cancer. Pharmaceutical compositions and methods of use are also included.

DETAILED DESCRIPTION OF THE INVENTION

The invention encompasses a genus of compounds of Formula I

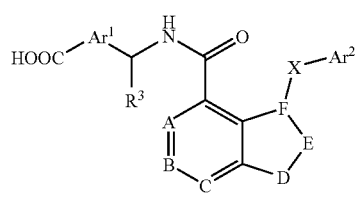

I or a pharmaceutically acceptable salt thereof, wherein:
each of A, B and C is independently selected from N, CH and $C(R^1)$;
-D-E-F- is selected from the group consisting of:
—$C(R^5)$=$C(R)$—N—,
—$C(R)$=N—$C(R)$—,
—$C(R)$=N—N—,
—N=$C(R)$—N—,
—N=N—N—,
—$C(R)_2$—N=C—,
—N(R)—$C(R)$=C—,
—N(R)—N=C—,
—O—N=C— and
—S—N=C—
wherein each R is independently selected from the group consisting of: hydrogen, $C_{1-4}$alkyl, $C_{1-4}$fluoroalkyl, $C_{1-4}$alkoxy, $C_{1-4}$fluoroalkoxy and acetyl;
$R^5$ is selected from the group consisting of: hydrogen, halo, $C_{1-4}$alkyl, $C_{1-4}$fluoroalkyl, $C_{1-4}$alkoxy, $C_{1-4}$fluoroalkoxy and acetyl;
X is a bond, —$CH_2$— or —$CH_2$—$CH_2$—, and X may additionally be —S— when -D-E-F- is —$C(R^5)$=N—$C(R)$—;
$Ar^1$ and $Ar^2$ are independently selected from the group consisting of: $C_{3-6}$cycloalkyl, aryl, heteroaryl and heterocyclyl, or a fused analog of $C_{3-6}$cycloalkyl, aryl, heteroaryl and heterocyclyl, wherein $Ar^2$ is optionally substituted with one to three $R^2$ groups and $Ar^1$ is optionally substituted with one to three $R^4$ groups; and
$R^1$, $R^2$, $R^3$ and $R^4$ are independently selected from the group consisting of: halo, $C_{1-4}$alkyl, $C_{1-4}$fluoroalkyl, $C_{1-4}$alkoxy, $C_{1-4}$fluoroalkoxy and acetyl. Multiple $R^1$, $R^2$ and $R^4$ may represent different members of the group, i.e., one $R^2$ group substituted on $Ar^2$ may be halo and another $R^2$ group substituted on $Ar^2$ may be $C_{1-4}$alkyl.

For purposes of this specification, the order of -D-E-F- for the listed members of the group should be read from left to right. For example, when -D-E-F- is —$C(R^5)$=$C(R)$—N—, D corresponds to —$C(R^5)$=, E corresponds to =$C(R)$— and F corresponds to —N—, such that the compound of Formula I is as follows:

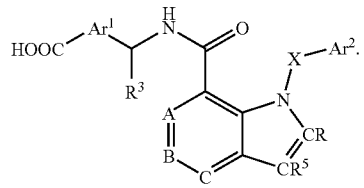

Within the genus, the invention encompasses a first sub-genus of compounds of Formula I wherein $R^3$ is methyl.

Also within the genus, the invention encompasses a second sub-genus of compounds of Formula I wherein $Ar^1$ is phenyl, optionally substituted with one to three $R^4$ groups.

Also within the genus, the invention encompasses a third sub-genus of compounds of Formula I wherein $Ar^2$ is phenyl, optionally substituted with one to three $R^2$ groups.

Also within the genus, the invention encompasses a fourth sub-genus of compounds of Formula I wherein each of A, B and C is independently selected from CH and $C(R^1)$.

Also within the genus, the invention encompasses a fifth sub-genus of compounds of Formula Ia

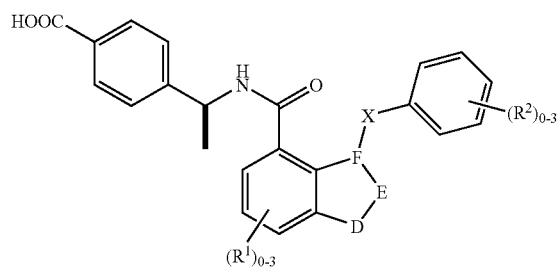

Ia or a pharmaceutically acceptable salt thereof, wherein:
-D-E-F- is selected from the group consisting of:
—C($R^5$)═C(R)—N—,
—C(R)═N—N—,
—N(R)—C(R)═C—,
—N═C(R)—N— and
—N═N—N—,
wherein each R is independently selected from the group consisting of: hydrogen, $C_{1-4}$alkyl, $C_{1-4}$fluoroalkyl, $C_{1-4}$alkoxy, $C_{1-4}$fluoroalkoxy and acetyl;
$R^5$ is selected from the group consisting of: hydrogen, halo, $C_{1-4}$alkyl, $C_{1-4}$fluoroalkyl, $C_{1-4}$alkoxy, $C_{1-4}$fluoroalkoxy and acetyl;
X is a bond or —$CH_2$—; and
$R^1$ and $R^2$ are independently selected from the group consisting of: halo, $C_{1-4}$alkyl, $C_{1-4}$fluoroalkyl, $C_{1-4}$alkoxy, $C_{1-4}$fluoroalkoxy and acetyl.

Within the fifth sub-genus, the invention encompasses a class of compounds of Formula Ia wherein X is —$CH_2$—.

Also within the fifth sub-genus, the invention encompasses a class of compounds of Formula Ia wherein: each R is independently selected from the group consisting of: hydrogen, methyl, thrifluoromethyl, trifluoromethoxy and acetyl; $R^5$ is selected from the group consisting of: hydrogen, chloro, methyl, thrifluoromethyl, trifluoromethoxy and acetyl; and $R^1$ and $R^2$ are independently selected from the group consisting of: chloro, methyl, thrifluoromethyl, trifluoromethoxy and acetyl.

Also within the fifth sub-genus, the invention encompasses a class of compounds of Formula Ia wherein -D-E-F- is —C($R^5$)═C(R)—N—.

Also within the fifth sub-genus, the invention encompasses a class of compounds of Formula Ia wherein -D-E-F- is —C(R)═N—N—.

Also within the fifth sub-genus, the invention encompasses a class of compounds of Formula Ia wherein -D-E-F- is: —N(R)—C(R)═C—.

Also within the fifth sub-genus, the invention encompasses a class of compounds of Formula Ia wherein -D-E-F- is —N═C(R)—N—.

Also within the fifth sub-genus, the invention encompasses a class of compounds of Formula Ia wherein -D-E-F- is —N═N—N—.

The invention also encompasses a compound selected from the following:
(1) 4-{(1S)-1-[({1-[3-(trifluoromethyl)benzyl]-1H-indol-7-yl}carbonyl)amino]ethyl}benzoic acid;
(2) 4-[(1S)-1-({[1-(3-chlorobenzyl)-1H-indol-7-yl]carbonyl}amino)ethyl]benzoic acid;
(3) 4-{(1S)-1-[({1-[3-chloro-4-(trifluoromethoxy)benzyl]-1H-indol-7-yl}carbonyl)amino]ethyl}benzoic acid;
(4) 4-{(1S)-1-[({1-[2-(3-chlorophenyl)ethyl]-1H-indol-7-yl}carbonyl)amino]ethyl}benzoic acid;
(5) 4-[(1S)-1-({[1-(3-chlorobenzyl)-3-methyl-1H-indol-7-yl]carbonyl}amino)ethyl]benzoic acid;
(6) 4-[(1S)-1-({[3-chloro-1-(3-chlorobenzyl)-1H-indol-7-yl]carbonyl}amino)ethyl]benzoic acid;
(7) 4-[(1S)-1-({[3-acetyl-1-(3-chlorobenzyl)-1H-indol-7-yl]carbonyl}amino)ethyl]benzoic acid;
(8) 4-[(1S)-1-({[5-chloro-1-(3-chlorobenzyl)-1H-indol-7-yl]carbonyl}amino)ethyl]benzoic acid;
(9) 4-[(1S)-1-({[5-chloro-1-(3-chlorobenzyl)-1H-indol-7-yl]carbonyl}amino)ethyl]benzoic acid;
(10) 4-[(1S)-1-({[1-(3-chlorobenzyl)-2-methyl-1H-indol-7-yl]carbonyl}amino)ethyl]benzoic acid;
(11) 4-[(1S)-1-({[1-(3-chlorobenzyl)-1H-indazol-7-yl]carbonyl}amino)ethyl]benzoic acid;
4-[(1S)-1-({[5-chloro-1-(3-chlorobenzyl)-1H-indazol-7-yl]carbonyl}amino)ethyl]benzoic acid;
(12) 4-{(1S)-1-[({3-[(3-chlorophenyl)thio]-1H-indol-4-yl}carbonyl)amino]ethyl}benzoic acid;
(13) 4-[(1S)-1-({[3-(3-chlorobenzyl)-1H-indol-4-yl]carbonyl}amino)ethyl]benzoic acid;
(14) 4-[(1S)-1-({[5-chloro-1-(3-chlorobenzyl)-1H-benzimidazol-7-yl]carbonyl}amino)ethyl]benzoic acid; and
(15) 4-[(1S)-1-({[5-chloro-1-(3-chlorobenzyl)-1H-1,2,3-benzotriazol-7-yl]carbonyl}amino)ethyl]benzoic acid;
or a pharmaceutically acceptable salt of any of the aforementioned.

The invention also encompasses a pharmaceutical composition comprising a compound of Formula I in admixture with one or more physiologically acceptable carriers or excipients.

The invention also encompasses a compound of Formula I or a pharmaceutically acceptable derivative thereof for use in human or veterinary medicine.

The invention also encompasses a method of treating a human or animal subject suffering from a condition which is mediated by the action of PGE2 at EP4 receptors, which method comprises administering to said subject an effective amount of a compound of Formula I.

The invention also encompasses the use of a compound of Formula I for the manufacture of a therapeutic agent for the treatment of a condition which is mediated by the action of PGE2 at EP4 receptors.

DEFINITIONS

"Alkyl", as well as other groups having the prefix "alk", such as alkoxy, alkanoyl, means carbon chains which may be linear or branched or combinations thereof. Examples of alkyl groups include methyl, ethyl, propyl, isopropyl, butyl, sec- and tert-butyl, pentyl, hexyl, heptyl, octyl, nonyl, and the like.

"Fluoroalkyl" means alkyl as defined above wherein one or more hydrogen atoms have been replaced by fluoro atoms.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means mono- or bicyclic saturated carbocyclic rings, each of which having from 3 to 10 carbon atoms. A "fused analog" of cycloalkyl means a monocyclic rings fused to an aryl or heteroaryl group in which the point of attachment is on the non-aromatic portion. Examples of cycloalkyl and fused analogs thereof include cyclopropyl, cyclobutyl, cyclopentyl, cyclohexyl, cycloheptyl, tetrahydronaphthyl, decahydronaphthyl, indanyl, and the like.

"Alkoxy" means alkoxy groups of a straight or branched having the indicated number of carbon atoms. $C_{1-6}$alkoxy, for example, includes methoxy, ethoxy, propoxy, isopropoxy, and the like.

"Cycloalkoxy" means cycloalkyl as defined above bonded to an oxygen atom, such as cyclopropyloxy.

"Fluoroalkoxy" means alkoxy as defined above wherein one or more hydrogen atoms have been replaced by fluoro atoms.

"Aryl" means mono- or bicyclic aromatic rings containing only carbon atoms. A "fused analog" of aryl means an aryl group fused to a monocyclic cycloalkyl or monocyclic heterocyclyl group in which the point of attachment is on the aromatic portion. Examples of aryl and fused analogs thereof include phenyl, naphthyl, indanyl, indenyl, tetrahydronaphthyl, 2,3-dihydrobenzofuranyl, dihydrobenzopyranyl, 1,4-benzodioxanyl, and the like.

"Heteroaryl" means a mono- or bicyclic aromatic ring containing at least one heteroatom selected from N, O and S, with each ring containing 5 to 6 atoms. A "fused analog" of heteroaryl means a heteroaryl group fused to a monocyclic cycloalkyl or monocyclic heterocyclyl group in which the point of attachment is on the aromatic portion. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzoxazolyl, benzothiazolyl, benzimidazolyl, benzofuranyl, benzothiophenyl, furo(2,3-b)pyridyl, quinolyl, indolyl, isoquinolyl, and the like.

"Heterocyclyl" means mono- or bicyclic saturated rings containing at least one heteroatom selected from N, S and O, each of said ring having from 3 to 10 atoms in which the point of attachment may be carbon or nitrogen. A "fused analog" of heterocyclyl means a monocyclic heterocycle fused to an aryl or heteroaryl group in which the point of attachment is on the non-aromatic portion. Examples of "heterocyclyl" and fused analogs thereof include pyrrolidinyl, piperidinyl, piperazinyl, imidazolidinyl, 2,3-dihydrofuro(2,3-b)pyridyl, benzoxazinyl, tetrahydroquinolinyl, tetrahydroisoquinolinyl, dihydroindolyl, and the like. The term also includes partially unsaturated monocyclic rings that are not aromatic, such as 2- or 4-pyridones attached through the nitrogen or N-substituted-(1H,3H)-pyrimidine-2,4-diones (N-substituted uracils).

"Halogen" and "halo" includes fluorine, chlorine, bromine and iodine.

Optical Isomers—Diastereomers—Geometric Isomers—Tautomers

Compounds of Formula I contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula I.

Compounds of the Formula I may be separated into diastereoisomeric pairs of enantiomers by, for example, fractional crystallization from a suitable solvent, for example MeOH or EtOAc or a mixture thereof. The pair of enantiomers thus obtained may be separated into individual stereoisomers by conventional means, for example by the use of an optically active amine as a resolving agent or on a chiral HPLC column.

Alternatively, any enantiomer of a compound of the general Formula I may be obtained by stereospecific synthesis using optically pure starting materials or reagents of known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methyl-glucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Utilities

The compounds of the invention are antagonists of the EP4 receptor and are therefore useful in treating EP4 receptor mediated diseases.

In view of their ability to bind to the EP4 receptor, the compounds of the invention are useful in the treatment of the disorders that follow. Thus, the compounds of the invention are useful as analgesics. For example they are useful in the treatment of chronic articular pain (e.g. rheumatoid arthritis, osteoarthritis, rheumatoid spondylitis, gouty arthritis and juvenile arthritis) including the property of disease modification and joint structure preservation; musculoskeletal pain; lower back and neck pain; sprains and strains; neuropathic pain; sympathetically maintained pain; myositis; pain associated with cancer and fibromyalgia; pain associated with migraine; pain associated with influenza or other viral infections, such as the common cold; rheumatic fever; pain associated with functional bowel disorders such as non-ulcer dyspepsia, non-cardiac chest pain and irritable bowel syndrome; pain associated with myocardial ischemia; post operative pain; headache; toothache; and dysmenorrhea.

The compounds of the invention are useful in the treatment of neuropathic pain. Neuropathic pain syndromes can develop following neuronal injury and the resulting pain may persist for months or years, even after the original injury has healed. Neuronal injury may occur in the peripheral nerves, dorsal roots, spinal cord or certain regions in the brain. Neuropathic pain syndromes are traditionally classified according to the disease or event that 25 precipitated them. Neuropathic pain syndromes include: diabetic neuropathy; sciatica; non-specific lower back pain; multiple sclerosis pain; fibromyalgia; HIV related neuropathy; post-herpetic neuralgia; trigeminal neuralgia; and pain resulting from physical trauma, amputation, cancer, toxins or chronic inflammatory conditions. These conditions are difficult to treat and although several drugs are known to have limited efficacy, complete pain control is rarely achieved. The symptoms of neuropathic pain are incredibly heterogeneous and are often described as spontaneous shooting and lancinating pain, or ongoing, burning pain. In addition, there is pain associated with normally non-painful sensations such as "pins and needles" (paraesthesias and dysesthesias), 35 increased sensitivity to touch (hyperesthes; a), painful sensation following innocuous stimulation (dynamic, static or thermal allodynia), increased sensitivity to noxious stimuli (thermal, cold, mechanical hyperalgesia), continuing pain sensation after removal of the stimulation (hyperpathia) or an absence of or deficit in selective sensory pathways (hypoalgesia).

The compounds of the invention are also useful in the treatment of inflammation, for example in the treatment of skin conditions (e.g. sunburn, burns, eczema, dermatitis, psoriasis); ophthalmic diseases such as glaucoma, retinitis, retinopathies, uveitis and of acute injury to the eye tissue (e.g. conjunctivitis); lung disorders (e.g. asthma, bronchitis, emphysema, allergic rhinitis, respiratory distress syndrome pigeon fancier's disease, farmer's lung, CORD); gastrointestinal tract disorders (e.g. aphthous ulcer, Crohn's disease, atopic gastritis, gastritis varialoforme, ulcerative colitis, coeliac disease, regional ileitis, irritable bowel syndrome, inflammatory bowel disease, gastrointestinal reflux disease); organ transplantation; other conditions with an inflammatory component such as vascular disease, migraine, periarteritis nodosa, thyroiditis, aplastic anaemia, Hodgkin's disease, sclerodoma, myaesthenia gravis, multiple sclerosis, sorcoidosis, nephrotic syndrome, Bechet's syndrome, polymyositis, gingivitis, myocardial ischemia, pyrexia, systemic lupus erythematosus, polymyositis, tendinitis, bursitis, and Sjogren's syndrome.

The compounds of the invention are also useful in the treatment of immunological diseases such as autoimmune diseases, immunological deficiency diseases or organ transplantation. The compounds of the invention are also effective in increasing the latency of HIV infection.

The compounds of the invention are also useful in the treatment of diseases of abnormal platelet function (e.g. occlusive vascular diseases).

The compounds of the invention are also useful for the preparation of a drug with diuretic action.

The compounds of the invention are also useful in the treatment of impotence or erectile dysfunction.

The compounds of the invention are also useful in the treatment of bone disease characterized by abnormal bone metabolism or resorption such as osteoporosis (especially postmenopausal osteoporosis), hyper-calcemia, hyperparathyroidism, Paget's bone diseases, osteolysis, hypercalcemia of malignancy with or without bone metastases, rheumatoid arthritis, periodontitis, osteoarthritis, ostealgia, osteopenia, cancer cacchexia, calculosis, lithiasis (especially urolithiasis), solid carcinoma, gout and ankylosing spondylitis, tendinitis and bursitis. In a further aspect compounds of the invention may be useful in inhibiting bone resorption and/or promoting bone generation.

The compounds of the invention are also useful for attenuating the hemodynamic side effects of NSAIDs and COX-2 inhibitors.

The compounds of the invention are also useful in the treatment of cardiovascular diseases such as hypertension or myocardiac ischemia; functional or organic venous insufficiency; varicose therapy; hemorrhoids; and shock states associated with a marked drop in arterial pressure (e.g. septic shock).

The compounds of the invention are also useful in the treatment of neurodegenerative diseases and neurodegeneration such as dementia, particularly degenerative dementia (including senile dementia, Alzheimer's disease, Pick's disease, Huntingdon's chores, Parkinson's disease and Creutzfeldt-Jakob disease, ALS, motor neuron disease); vascular dementia (including multi-infarct dementia); as well as dementia associated with intracranial space occupying lesions; trauma; infections and related conditions (including HIV infection); metabolism; toxins; anoxia and vitamin deficiency; and mild cognitive impairment associated with ageing, particularly Age Associated Memory Impairment.

The compounds of Formula I are also useful in the treatment of neuroprotection and in the treatment of neurodegeneration following stroke, cardiac arrest, pulmonary bypass, traumatic brain injury, spinal cord injury or the like.

The compounds of the invention are also useful in the treatment of tinnitus.

The compounds of the invention are also useful in preventing or reducing dependence on, or preventing or reducing tolerance or reverse tolerance to, a dependence-inducing agent. Examples of dependence inducing agents include opioids (e.g. morphine), CNS depressants (e.g. ethanol), psychostimulants (e.g. cocaine) and nicotine.

The compounds of the invention are also useful in the treatment of complications of Type 1 diabetes (e.g. diabetic microangiopathy, diabetic retinopathy, diabetic nephropathy, macular degeneration, glaucoma), nephrotic syndrome, aplastic anaemia, uveitis, Kawasaki disease and sarcoidosis.

The compounds of the invention are also useful in the treatment of kidney dysfunction (nephritis, particularly mesangial proliferative glomerulonephritis, nephritic syndrome), liver dysfunction (hepatitis, cirrhosis), gastrointestinal dysfunction (diarrhea) and colon cancer.

The compounds of the invention are also useful for treating or preventing a neoplasia in a subject in need of such treatment or prevention. The term "treatment" includes partial or total inhibition of the neoplasia growth, spreading or metastasis, as well as partial or total destruction of the neoplastic cells. The term "prevention" includes either preventing the onset of clinically evident neoplasia altogether or preventing the onset of a preclinically evident stage of neoplasia in individuals at risk. Also intended to be encompassed by this definition is the prevention of initiation for malignant cells or to arrest or reverse the progression of premalignant cells to malignant cells. This includes prophylactic treatment of those at risk of developing the neoplasia. The term "subject" for purposes of treatment includes any human or mammal subject who has any one of the known neoplasias, and preferably is a human subject. For methods of prevention, the subject is any human or animal subject, and preferably is a human subject who is at risk for obtaining a neoplasia. The subject may be at risk due to exposure to carcinogenic agents, being genetically predisposed to have the neoplasia, and the like.

The term "neoplasia" includes both benign and cancerous tumors, growths and polyps. Thus, the compounds of the invention are useful for treating or preventing benign tumors, growths and polyps including squamous cell papilloma, basal cell tumor, transitional cell papilloma, adenoma, gastrinoma, cholangiocellular adenoma, hepatocellular adenoma, renal tubular adenoma, oncocytoma, glomus tumor, melanocytic nevus, fibroma, myxoma, lipoma, leiomyoma, rhabdomyoma, benign teratoma, hemangioma, osteoma, chondroma and meningioma. The compounds of the invention are also useful for treating or preventing cancerous tumors, growths and polyps including squamous cell carcinoma, basal cell carcinoma, transitional cell carcinoma, adenocarcinoma, malignant gastrinoma, cholangiocellular carcinoma, hepatocellular carcinoma, renal cell carcinoma, malignant melanoma, fibrosarcoma, myxosarcoma, liposarcoma, leiomyosarcoma, rhabdomyosarcoma, malignant teratoma, hemangiosarcoma, Kaposi sarcoma, lymphangiosarcoma, osterosarcoma, chondrosarcoma, malignant meningioma, non-Hodgkin lymphoma, Hodgkin lymphoma and leukemia. For purposes of this specification, "neoplasia" includes brain cancer, bone cancer, epithelial cell-derived neoplasia (epithelial carcinoma), basal cell carcinoma, adenocarcinoma, gastrointestinal cancer such as lip cancer, mouth cancer, esophogeal cancer, small bowel cancer and stomach cancer, colon cancer, rectal cancer, liver cancer, bladder cancer, pancreas cancer, ovary cancer, cervical cancer, lung cancer, breast cancer and skin cancer, such as squamus cell and basal cell cancers, prostate cancer, renal cell carcinoma, and other known cancers that affect epithelial, mesenchymal or blood cells throughout the body. The compounds of the invention are useful for treating or preventing any of the aforementioned cancers. The compounds of the invention are useful for treating or preventing benign and cancerous tumors, growths and polyps of the following cell types: squamous epithelium, basal cells, transitional epithelium, glandular epithelium, G cells, bile ducts epithelium, hepatocytes, tubules epithelium, melanocytes, fibrous connective tissue, cardiac skeleton, adipose tissue, smooth muscle, skeletal muscle, germ cells, blood vessels, lymphatic vessels, bone, cartilage, meninges, lymphoid cells and hematopoietic cells. The compounds can be used to treat subjects having adenomatous polyps, including those with familial adenomatous polyposis (FAP). Additionally, the compounds can be used to prevent polyps from forming in patients at risk of FAP. Preferably, the compounds of the invention are useful for treating or preventing the following cancers: colorectal, esophagus stomach, breast, head and neck, skin, lung, liver, gall bladder, pancreas, bladder, endometrium cervix, prostate, thyroid and brain.

It is to be understood that reference to treatment includes both treatment of established symptoms and prophylactic treatment, unless explicitly stated otherwise.

Dose Ranges

The magnitude of prophylactic or therapeutic dose of a compound of Formula I will, of course, vary with the nature and severity of the condition to be treated, and with the particular compound of Formula I used and its route of administration. The dose will also vary according to the age, weight and response of the individual patient. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

For use where a composition for intravenous administration is employed, a suitable dosage range is from about 0.01 mg to about 25 mg (preferably from 0.1 mg to about 10 mg) of a compound of Formula I per kg of body weight per day.

In the case where an oral composition is employed, a suitable dosage range is, e.g. from about 0.01 mg to about 100 mg of a compound of Formulas I or I a per kg of body weight per day, preferably from about 0.1 mg to about 10 mg per kg.

For use where a composition for sublingual administration is employed, a suitable dosage range is from 0.01 mg to about 25 mg (preferably from 0.1 mg to about 5 mg) of a compound of Formula I per kg of body weight per day.

Pharmaceutical Compositions

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

Any suitable route of administration may be employed for providing a mammal, especially a human with an effective dosage of a compound of the present invention. For example, oral, sublingual, rectal, topical, parenteral, ocular, pulmonary, nasal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, sublingual, rectal, topical, parenteral (including subcutaneous, intramuscular, and intravenous), ocular (ophthalmic), pulmonary (aerosol inhalation), or nasal administration, although the most suitable route in my given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulizers. The compounds may also be delivered as powders which may be formulated and the powder composition may be inhaled with the aid of an insufflation powder inhaler device. The preferred delivery systems for inhalation are metered dose inhalation (MDI) aerosol, which may be formulated as a suspension or solution of a compound of Formula I in suitable propellants, such as fluorocarbons or hydrocarbons and dry powder inhalation (DPI) aerosol, which may be formulated as a dry powder of a compound of Formula I with or without additional excipients.

Suitable topical formulations of a compound of formula I include transdermal devices, aerosols, creams, ointments, lotions, dusting powders, and the like.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 1 mg to about 500 mg of the active ingredient and each cachet or capsule contains from about 1 to about 500 mg of the active ingredient.

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I, either administered separately or in the same pharmaceutical compositions, include, but are not limited to: COX-2 inhibitors, such as celecoxib, rofecoxib, etoricoxib, valdecoxib or parecoxib; 5-lipoxygenase inhibitors; NSAIDs, such as diclofenac, indomethacin, nabumetone or ibuprofen; leukotriene receptor antagonists; DMARDs such as methotrexate; adenosine A1 receptor agonists; sodium channel blockers, such as lamotrigine; NMDA receptor modulators, such as glycine receptor antagonists; gabapentin and related compounds; tricyclic antidepressants such as amitriptyline; neurone stabilising antiepileptic drugs; monoaminergic uptake inhibitors such as venlafaxine; opioid analgesics; local anaesthetics; 5HT agonists, such as triptans, for example sumatriptan, naratriptan, zolmitriptan, eletriptan, frovatriptan, almotriptan or rizatriptan; EP1 receptor ligands; EP2 receptor ligands; EP3 receptor ligands; EP1 antagonists; EP2 antagonists and EP3 antagonists. When the compounds are used in combination with other therapeutic agents, the compounds may be administered either sequentially or simultaneously by any convenient route.

The invention thus provides, in a further aspect, a combination comprising a compound of Formula I or a pharmaceutically acceptable derivative thereof together with a further therapeutic agent or agents.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

The weight ratio of the compound of the Formula I to the second active ingredient may be varied and will depend upon the effective dose of each ingredient. Generally, an effective dose of each will be used. Thus, for example, when a compound of Formula I is combined with an NSAID the weight ratio of the compound of Formula I to the NSAID will generally range from about 1000:1 to about 1:1000, preferably about 200:1 to about 1:200. Combinations of a compound of Formula I and other active ingredients will generally also be within the aforementioned range, but in each case, an effective dose of each active ingredient should be used.

Assays for Determining Biological Activity

The compounds of Formula I can be tested using the following assays to determine their prostanoid antagonist or agonist activity in vitro and in vivo and their selectivity. The prostaglandin receptor activities demonstrated are DP, $EP_1$, $EP_2$, $EP_3$, $EP_4$, FP, IP and TP.

Stable Expression of Prostanoid Receptors in the Human Embryonic Kidney (HEK) 293(ebna) Cell Line Prostanoid receptor cDNAs corresponding to full length coding sequences are subcloned into the appropriate sites of mammalian expression vectors and transfected into HEK 293 (ebna) cells. HEK 293(ebna) cells expressing the individual cDNAs are grown under selection and individual colonies are isolated after 2-3 weeks of growth using the cloning ring method and subsequently expanded into clonal cell lines.

Prostanoid Receptor Binding Assays

Transfected HEK 293(ebna) cells are maintained in culture, harvested and membranes are prepared by differential centrifugation, following lysis of the cells in the presence of protease inhibitors, for use in receptor binding assays. Prostanoid receptor binding assays (for DP1, DP2 (CRTH2), EP1, EP2, EP3-III, EP4, FP, IP, and TP) are performed in 10 mM MES/KOH (pH 6.0) (EPs, FP and TP) or 10 mM HEPES/ KOH (pH 7.4) (DPs and IP), containing 1 mM EDTA, 2.5-30 mM divalent cation and the appropriate radioligand. Synthetic compounds are added in dimethylsulfoxide which is kept constant at 1% (v/v) in all incubations. The reaction is initiated by addition of membrane protein. Non-specific binding is determined in the presence of 10 µM of the corresponding non-radioactive prostanoid. Incubations are conducted for 60-90 min at room temperature or 30° C. and terminated by rapid filtration. Specific binding is calculated by subtracting non specific binding from total binding. The residual specific binding at each ligand concentration is calculated and expressed as a function of ligand concentration in order to construct sigmoidal concentration-response curves. The binding affinity of the compounds is determined by calculating the equilibrium inhibition constant ($K_i$) from the equation $K_i=\text{InPt}/1+[\text{radioligand}]/K_d$ where $K_d$ is the equilibrium dissociation constant for the radioligand:receptor interaction and InPt is the inflection point of the dose-response curves.

Examples 1 to 16 were tested in the above binding assay for the EP4 receptor and demonstrated $IC_{50}$s of less than 500 nM.

Prostanoid Receptor Agonist and Antagonist Assays

Whole cell second messenger assays measuring stimulation of intracellular cAMP accumulation in HEK-293(ebna)- hEP4 cells are performed to determine whether receptor ligands are agonists or antagonists. Cells are harvested and resuspended in HBSS containing 25 mM HEPES, pH 7.4. Incubations contain 0.5 mM IBMX (phosphodiesterase inhibitor, available from Biomol). Samples are incubated at 37° C. for 10 min, the reaction is terminated and cAMP levels are then measured. Ligands are added in dimethylsulfoxide which is kept constant at 1% (v/v; agonists) or 2% (v/v; antagonists) in all incubations. For agonists, second messenger responses are expressed as a function of ligand concentration and both $EC_{50}$ values and the maximum response as compared to a $PGE_2$ standard are calculated. For antagonists, the ability of a ligand to inhibit an agonist response is determined by carrying out dose-response curves in the presence of $PGE_2$ agonist at a concentration corresponding to its $EC_{70}$. $IC_{50}$ values are calculated as the concentration of ligand required to inhibit 50% of the $PGE_2$-induced activity.

In the EP4 receptor antagonist assay, the compounds of Examples 1 to 16 showed an $EC_{50} \leq 500$ nM.

Rat Paw Edema Assay

The method is the same as described in Chan et al (J. Pharmacol. Exp. Ther. 274: 1531-1537, 1995).

Acute Inflammatory Hyperalgesia Induced by Carrageenan in Rats

The method is the same as described in Boyce et al (Neuropharmacology 33: 1609-1611, 1994).

Adjuvant-Induced Arthritis in Rats

Female Lewis rats (body weight ~146-170 g) are weighed, ear marked, and assigned to groups (a negative control group in which arthritis was not induced, a vehicle control group, a positive control group administered indomethacin at a total daily dose of 1 mg/kg and four groups administered with a test compound at total daily doses of 0.10-3.0 mg/kg) such that the body weights were equivalent within each group. Six groups of 10 rats each are injected into a hind paw with 0.5 mg of *Mycobacterium butyricum* in 0.11 mL of light mineral oil (adjuvant), and a negative control group of 10 rats was not injected with adjuvant. Body weights, contralateral paw volumes (determined by mercury displacement plethysmography) and lateral radiographs (obtained under Ketamine and Xylazine anesthesia) are determined before (day-1) and 21 days following adjuvant injection, and primary paw volumes are determined before (day-1) and on days 4 and 21 following adjuvant injection. The rats are anesthetized with an intramuscular injection of 0.03-0.1 mL of a combination of Ketamine (87 mg/kg) and Xylazine (13 mg/kg) for radiographs and injection of adjuvant. The radiographs are made of both hind paws on day 0 and day 21 using the Faxitron (45 kVp, 30 seconds) and Kodak X-OMAT TL film, and are developed in an automatic processor. Radiographs are evaluated for changes in the soft and hard tissues by an investigator who was blinded to experimental treatment. The following radiographic changes are graded numerically according to severity: increased soft issue volume (0-4), narrowing or widening of joint spaces (0-5) subchondral erosion (0-3), periosteal reaction (0-4), osteolysis (0-4) subluxation (0-3), and degenerative joint changes (0-3). Specific criteria are used to establish the numerical grade of severity for each radiographic change. The maximum possible score per foot was 26. A test compound at total daily doses of 0.1, 0.3, 1, and 3 mg/kg/day, indomethacin at a total daily dose of 1 mg/kg/day, or vehicle (0.5% methocel in sterile water) are administered per os b.i.d. beginning post injection of adjuvant and continuing for 21 days. The compounds are prepared weekly, refrigerated in the dark until used, and vortex mixed immediately prior to administration.

Method of Synthesis

Scheme 1

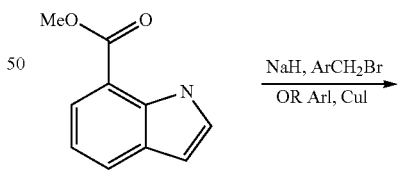

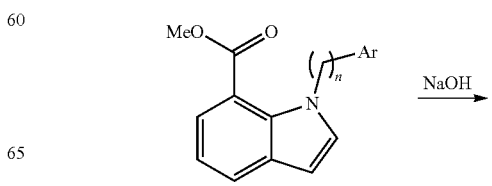

-continued
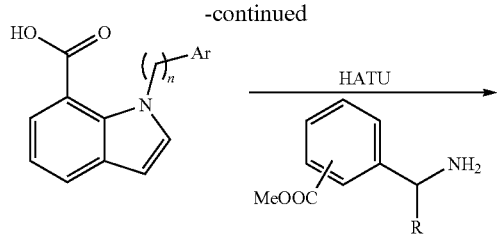
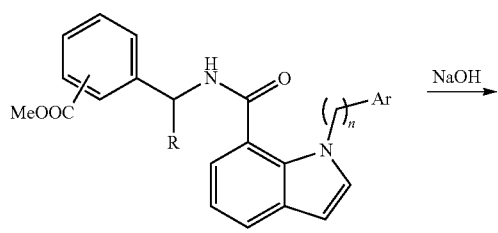
n = 0, 1, 2
Scheme 2:
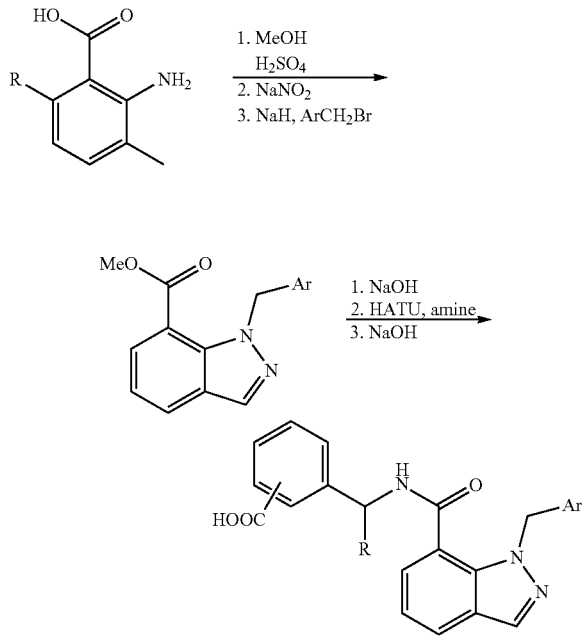
Scheme 3:
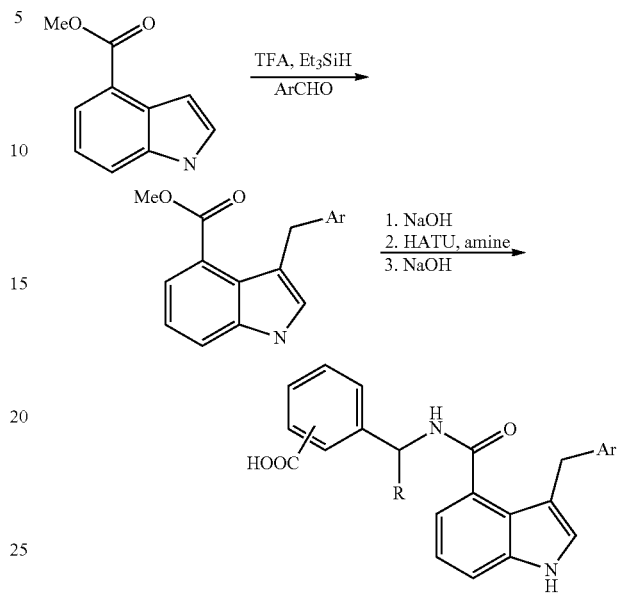
Scheme 4:
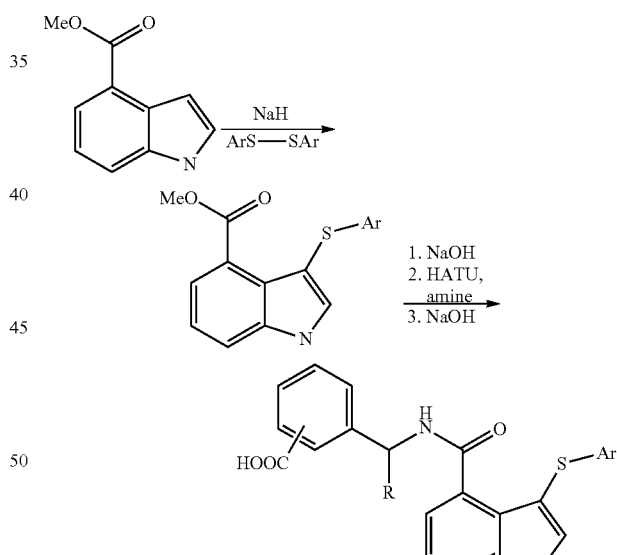
Scheme 5:
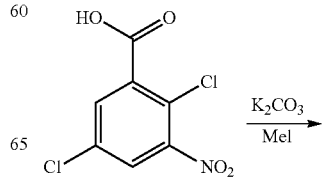

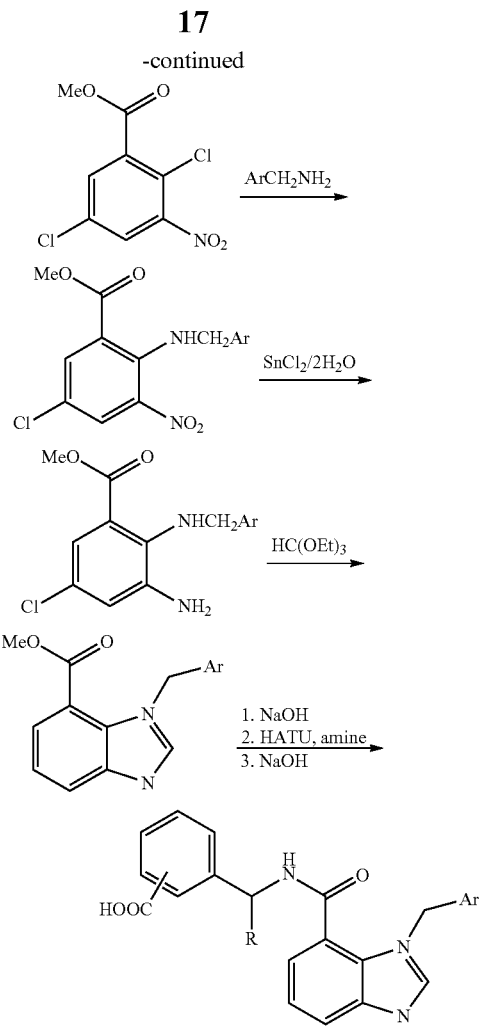

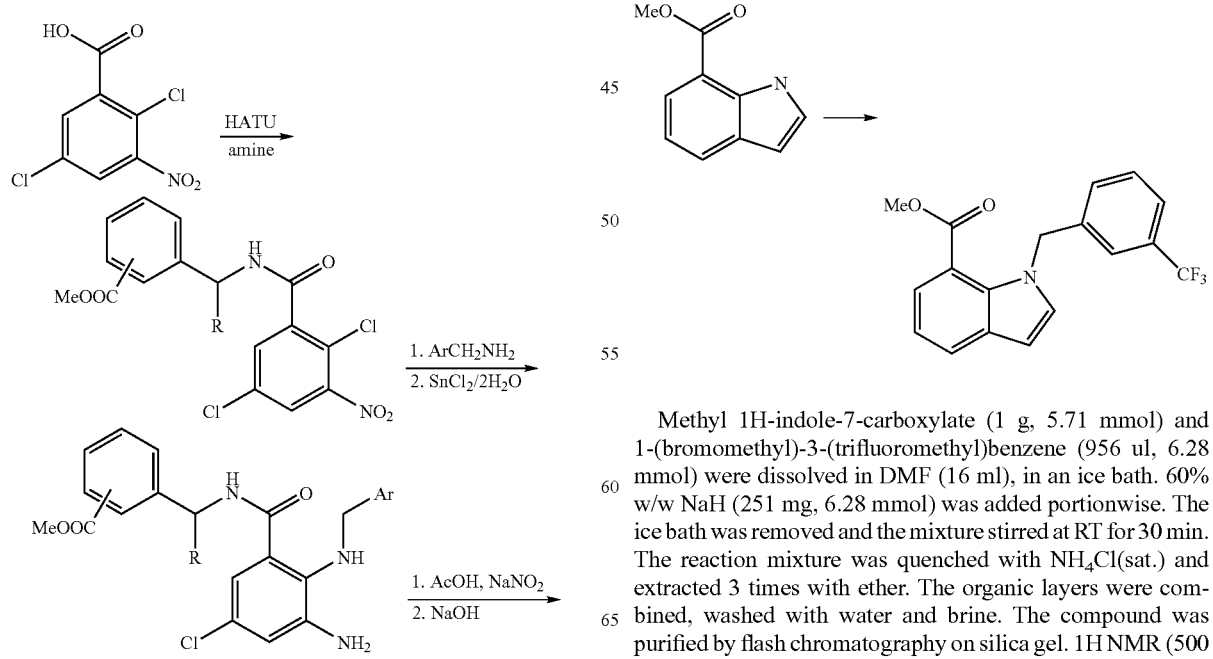

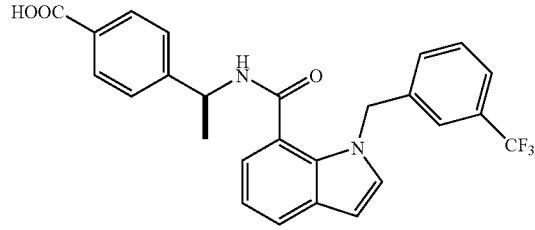

In the above schemes, the designation Ar corresponds to Ar² in Formula I and is optionally substituted as described herein.

Example 1

4-{(1S)-1-[({1-[3-(trifluoromethyl)benzyl]-1H-indol-7-yl}carbonyl)amino]ethyl}benzoic acid Step 1: methyl 1-[3-(trifluoromethyl)benzyl]-1H-indole-7-carboxylate Methyl 1H-indole-7-carboxylate (1 g, 5.71 mmol) and 1-(bromomethyl)-3-(trifluoromethyl)benzene (956 ul, 6.28 mmol) were dissolved in DMF (16 ml), in an ice bath. 60% w/w NaH (251 mg, 6.28 mmol) was added portionwise. The ice bath was removed and the mixture stirred at RT for 30 min. The reaction mixture was quenched with NH₄Cl(sat.) and extracted 3 times with ether. The organic layers were combined, washed with water and brine. The compound was purified by flash chromatography on silica gel. 1H NMR (500 MHz, DMSO-d6): δ 7.40 (d, 1H), 7.25 (s, 1H), 7.10 (m, 1H), 7.00 (m, 2H), 6.75 (s, 1H), 6.65 (t, 1H), 6.50 (d, 1H), 6.25 (s, 1H), 5.25 (s, 2H), 2.05 (d, 3H).

Step 2 and Step 3: methyl 4-{(1S)-1-[({1-[3-(trifluoromethyl)benzyl]-1H-indol-7-yl}carbonyl)amino]ethyl}benzoate

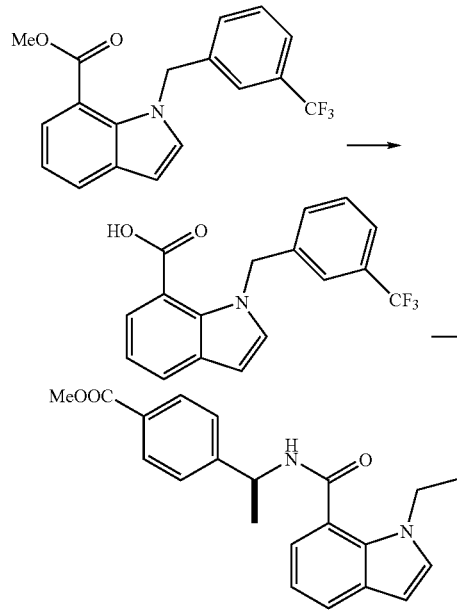

Methyl 1-[3-(trifluoromethyl)benzyl]-1H-indole-7-carboxylate (1.4 g, 4.2 mmol) was dissolved in THF (4.2 ml) and MeOH (2.1 ml). 2M NaOH (2.1 ml, 4.2 mmol) was added and the mixture stirred at 50° C. overnight. The mixture was cooled, the organic solvents removed and poured into 1N HCl. The resulting solid was filtered and washed with water. To an ice bath cooled mixture of the resulting solid, HATU (262 mg, 0.689 mmol) and (1S)-1-[4-(methoxycarbonyl)phenyl]ethanaminium chloride (168 mg, 0.939 mmol) was added acetonitrile (4.2 ml) and DIPEA (272 ul, 1.56 mmol). The ice bath was removed and the mixture stirred for 2 hours at RT. The solvent was removed and the crude mixture purified by flash chromatography on silica gel. 1H NMR (500 MHz, DMSO-d6): δ 8.95 (d, 1H), 7.90 (d, 2H), 7.75 (d, 1H), 7.60-7.50 (m, 2H), 7.50-7.40 (m, 3H), 7.20 (m, 2H), 7.10 (t, 1H), 7.00 (d, 1H), 6.65 (s, 1H), 5.60 (dd, 2H), 5.00 (m, 1H), 3.85 (s, 3H), 1.20 (d, 3H).

Step 4: 4-{(1S)-1-[({1-[3-(trifluoromethyl)benzyl]-1H-indol-7-yl}carbonyl)amino]ethyl}benzoic acid

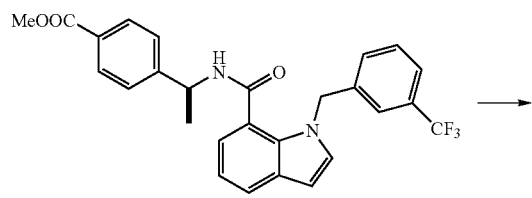

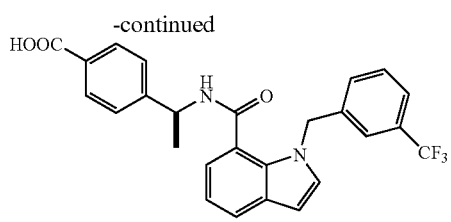

Methyl 4-{(1S)-1-[({1-[3-(trifluoromethyl)benzyl]-1H-indol-7-yl}carbonyl)amino]ethyl}benzoate (220 mg, 0.458 mmol) was dissolved in THF (2 ml) and MeOH (1.14 ml). 2M NaOH (1.14 ml, 2.29 mmol) was added and the mixture stirred at 50° C. for 1 hour. The mixture was cooled, the organic solvents removed and poured into 1N HCl. The resulting solid was filtered and washed with water. 1H NMR (500 MHz, DMSO-d6): δ 12.90 (bs, 1H), 8.90 (d, 1H), 7.85 (d, 2H), 7.75 (d, 1H), 7.65-7.55 (m, 2H), 7.50-7.40 (m, 3H), 7.25 (m, 2H), 7.15-7.00 (m, 4H), 7.00 (d, 1H), 6.65 (s, 1H), 5.60 (dd, 2H), 5.00 (m, 1H), 1.20 (d, 3H). MS-ESI (464.9).

The following Examples 2 through 10 can be made in accordance with Scheme 1 and Example 1 with the appropriate modifications.

Example 2

4-[(1S)-1-({[1-(3-chlorobenzyl)-1H-indol-7-yl]carbonyl}amino)ethyl]benzoic acid

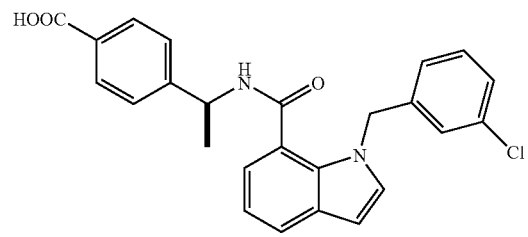

The title compound may be made in accordance with Example 1 with the appropriate modifications.

1H NMR (500 MHz, Acetone-d6): δ 8.00 (d, 2H), 7.95 (d, 1H), 7.74 (d, 1H), 7.55 (d, 2H), 7.46 (s, 1H), 7.29 (d, 1H), 7.24 (s, 1H), 7.23 (s, 1H), 7.08 (t, 1H), 6.89 (s, 1H), 6.85 (m, 1H), 6.65 (s, 1H), 5.73 (d, 1H), 5.58 (d, 1H), 5.72 (m, 1H), 1.42 (d, 3H).

Example 3

4-[(1S)-1-({[1-(3-chlorophenyl)-1H-indol-7-yl]carbonyl}amino)ethyl]benzoic acid

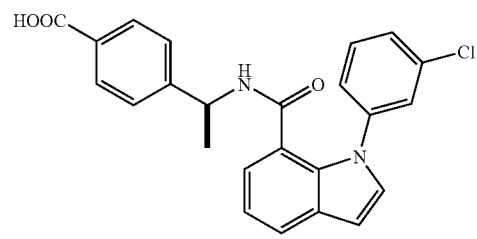

Step 1 Methyl 1-(3-chlorophenyl)-1H-indole-7-carboxylate

A mixture of methyl 1H-indole-7-carboxylate (0.175 g), 3-iodo-chlorobenzene (0.358 g), Cs$_2$CO$_3$ (0.490 g), CuCl (0.099 g), and 2,2,6,6-tetramethyl-3,5-heptanedione (0.04 mL) in 5 mL of N-methylpyrrolidine was heated at 120° C. for 3 days. The mixture was then diluted with 50 mL of EtOAc and filtered through a pad of silica gel. The filtrate was washed with 3×15 mL of water and dried over Na$_2$SO$_4$. After filtration and concentration, the residue was purified by Combiflash eluted with a gradient of EtOAc/hexane to give 0.1 g of the title compound.

1H NMR (500 MHz, Acetone-d6): δ 7.90 (d, 1H), 7.58 (d, 2H), 7.50-7.58 (m, 2H), 7.41-7.46 (m, 2H), 7.23 (d, 1H), 7.25 (t, 1H), 6.83 (s, 1H).

Step 2 1-(3-Chlorophenyl)-1H-indole-7-carboxylic acid

A mixture of the product of Step 1 (0.1 g) and LiOH (3 mL, 1N) in 15 mL of 1:1:1 THF/MeOH/H$_2$O was stirred for two days at room temperature and heated at 55° C. for 20 h. The mixture was cooled and treated with 5 mL of 1N HCl, followed by extraction with 30 mL of EtOAc. The EtOAc extract was dried over Na$_2$SO$_4$, filtered and concentrated to give the crude product (0.1 g) which was used for next step without further purification.

Step 3 4-[(1S)1-({[1-(3-Chlorophenyl)-1H-indol-7-yl]carbonyl}amino)ethyl]benzoic acid From the crude product of Step 3 (0.1 g), the title compound was prepared as a white solid (0.11 g) by using the same procedure as described in Step 3 and 4 for Example 1. 1H NMR (500 MHz, Acetone-d6): δ 8.00 (s, 2H), 7.89 (d, 1H), 7.75 (d, 1H), 7.48 (d, 2H), 7.49 (d, 1H), 7.30-7.40 (m, 3H), 7.19 (t, 1H), 7.78 (s, 1H), 4.85 (m, 1H), 1.36 (d, 3H).

The following Examples 4 through 10 can be made in accordance with Example 1 with the appropriate modifications.

Example 4

4-{(1S)-1-[({1-[3-chloro-4-(trifluoromethoxy)benzyl]-1H-indol-7-yl}carbonyl)amino]ethyl}benzoic acid

$^1$H NMR (400 MHz, DMSO): δ 12.75 (bs, 1H), 9.95 (d, 1H), 7.90 (d, 2H), 7.75 (d, 1H), 7.55 (d, 1H), 7.45 (d, 2H), 7.35 (d, 1H), 7.25 (d, 1H), 7.15 (t, 1H), 7.05 (s, 1H), 6.85 (d, 1H), 6.65 (s, 1H), 5.50 (dd, 2H), 5.05 (m, 1H), 1.25 (d, 3H). MS-ESI (514.9).

Example 5

4-{(1S)-1-[({1-[2-(3-chlorophenyl)ethyl]-1H-indol-7-yl}carbonyl)amino]ethyl}benzoic acid

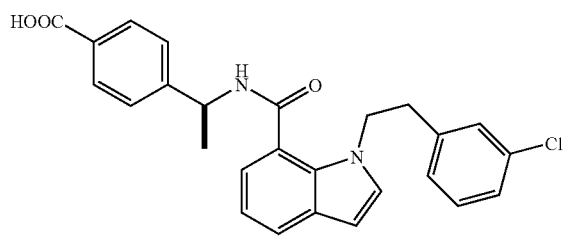

$^1$H NMR (400 MHz, DMSO): δ 12.80 (bs, 1H), 9.20 (d, 1H), 7.90 (d, 2H), 7.65 (d, 10H), 7.55 (d, 2H), 7.30-7.15 (m, 4H), 7.15 (t, 2H), 7.25 (d, 1H), 6.95 (d, 1H), 6.55 (s, 1H), 5.30 (m, 1H), 4.35 (t, 2H), 2.80 (m, 2H), 1.45 (d, 3H). MS-ESI (445.1).

Example 6

4-[(1S)-1-({[1-(3-chlorobenzyl)-3-methyl-1H-indol-7-yl]carbonyl}amino)ethyl]benzoic acid

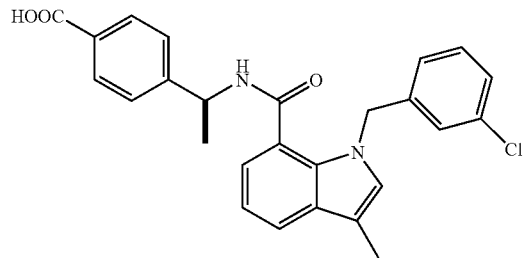

$^1$H NMR (400 MHz, DMSO): δ 12.85 (bs, 1H), 8.90 (d, 1H), 7.90 (d, 2H), 7.75 (d, 1H), 7.45 (d, 2H), 7.30-7.20 (m, 4H), 7.10 (t, 1H), 6.90 (s, 1H), 6.75 (d, 1H), 6.65 (s, 1H), 5.45 (dd, 2H), 5.05 (m, 1H), 2.30 (s, 3H), 1.30 (d, 3H). MS-ESI (447.0).

Example 7

4-[(1S)-1-({[3-chloro-1-(3-chlorobenzyl)-1H-indol-7-yl]carbonyl}amino)ethyl]benzoic acid

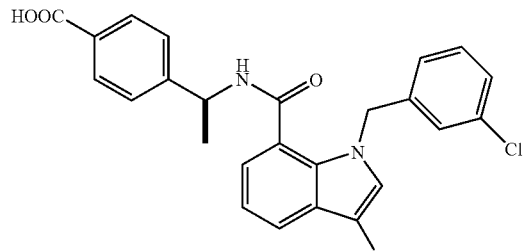

¹H NMR (400 MHz, DMSO): δ 12.80 (bs, 1H), 9.00 (d, 1H), 7.85 (d, 2H), 7.80 (d, 1H), 7.65 (d, 1H), 7.45 (d, 2H), 7.40-7.20 (m, 4H), 6.90 (s, 1H), 6.75 (d, 1H), 5.50 (dd, 2H), 5.05 (m, 1H), 1.30 (d, 3H). MS-ESI (464.9).

Example 8

4-[(1S)-1-({[3-acetyl-1-(3-chlorobenzyl)-1H-indol-7-yl]carbonyl}amino)ethyl]benzoic acid

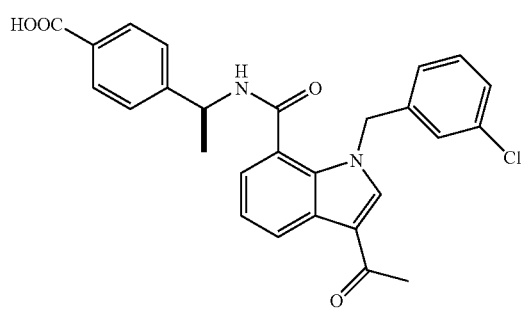

¹H NMR (400 MHz, DMSO): δ 12.80 (bs, 1H), 9.00 (d, 1H), 8.60 (s, 10H), 8.40 (d, 1H), 7.90 (d, 2H), 7.40 (d, 2H), 7.40-7.20 (m, 4H), 7.00 (s, 1H), 6.80 (d, 1H), 5.60 (dd, 2H), 5.00 (m, 1H), 1.25 (d, 3H). MS-ESI (475.0).

Example 9

4-[(1S)-1-({[5-chloro-1-(3-chlorobenzyl)-1H-indol-7-yl]carbonyl}amino)ethyl]benzoic acid

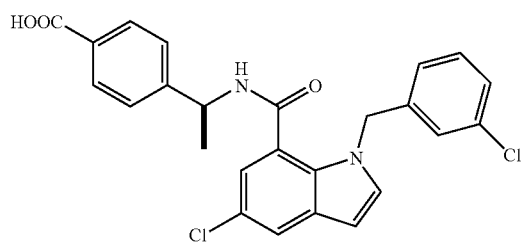

4-[(1S)-1-({[5-chloro-1-(3-chlorobenzyl)-1H-indol-7-yl]carbonyl}amino)ethyl]benzoic acid ¹H NMR (400 MHz, DMSO): δ 12.85 (bs, 1H), 9.05 (d, 1H), 7.85 (d, 2H), 7.80 (s, 1H), 7.60 (s, 1H), 7.40 (d, 2H), 7.30-7.15 (m, 3H), 6.80 (s, 1H), 6.70 (d, 1H), 6.60 (s, 1H), 5.50 (dd, 2H), 5.00 (m, 1H), 1.25 (d, 3H). MS-ESI (465.0).

Example 10

4-[(1S)-1-({[1-(3-chlorobenzyl)-2-methyl-1H-indol-7-yl]carbonyl}amino)ethyl]benzoic acid

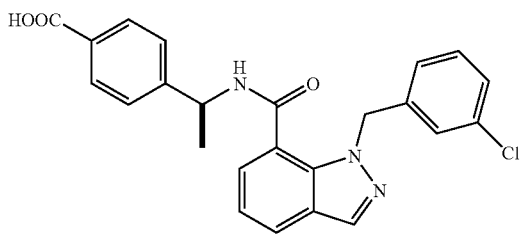

4-[(1S)-1-({[1-(3-chlorobenzyl)-2-methyl-1H-indol-7-yl]carbonyl}amino)ethyl]benzoic acid ¹H NMR (400 MHz, DMSO): δ 12.80 (bs, 1H), 8.90 (d, 1H), 7.80 (d, 2H), 7.60 (d, 1H), 7.35 (d, 2H), 7.30-7.20 (m, 2H), 7.15-7.00 (m, 2H), 6.70 (s, 1H), 6.65 (d, 1H), 6.45 (s, 1H), 5.50 (dd, 2H), 5.05 (m, 1H), 2.30 (s, 3H), 1.20 (d, 3H). MS-ESI (445.0).

Example 11

4-[(1S)-1-({[1-(3-chlorobenzyl)-1H-indazol-7-yl]carbonyl}amino)ethyl]benzoic acid

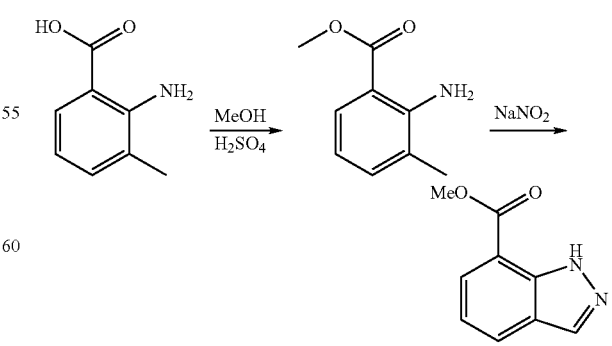

Step 1 and 2: methyl 1H-indazole-7-carboxylate

To a solution of 2-amino-3-methylbenzoic acid (25 g, 165 mmol) in 500 mL of MeOH, was slowly added concentrated sulfuric acid (100 mL, 1654 mmol) afterwhich the solution was refluxed overnight. After cooling to 0° C. and neutralization by slow addition with sodium carbonate the solution was extracted with EtOAc. The organic phases were then combined, washed with brine, dried over MgSO4, filtered and concentrated in vacuo. The methyl ester was purified by flash chromatography using 5-25% EtOAc/hexanes to yield 13 g of pure ester. 1H NMR (500 MHz, CDCl$_3$): δ7.8 (d, 1H), 7.2 (d, 1H), 6.6 (t, 1H), 5.9 (bs, 2H), 3.9 (s, 3H), 2.2 (s, 3H).

To a solution of methyl 2-amino-3-methylbenzoate (13 g, 78.7 mmol) in 500 mL of AcOH at 0° C. was slowly added a solution of sodium nitrite (6.5 g, 94.2 mmol) in 100 mL of water dropwise over 1 hour. The solution was allowed to stir for ON at rt afterwhich it was concentrated to one tenth its volume and then neutralized by the slow addition of 5% ammonium hydroxide. The solution was then extracted with EtOAc and the organic phases were then combined, washed with brine, dried over MgSO4, filtered and concentrated in vacuo. The indazole-methyl ester was purified by flash chromatography using 5-25% EtOAc/hexanes to yield 10 g of pure ester. $^1$H NMR (500 MHz, CDCl$_3$): δ 12.5 (bs, 1H), 8.2 (s, 1H), 8.1 (m, 2H), 7.3 (t, 1H), 4.09 (s, 3H). LRMS M+1 177.1.

Step 3: 4-[(1S)-1-({[1-(3-chlorobenzyl)-1H-indazol-7-yl]carbonyl}amino)ethyl]benzoic acid

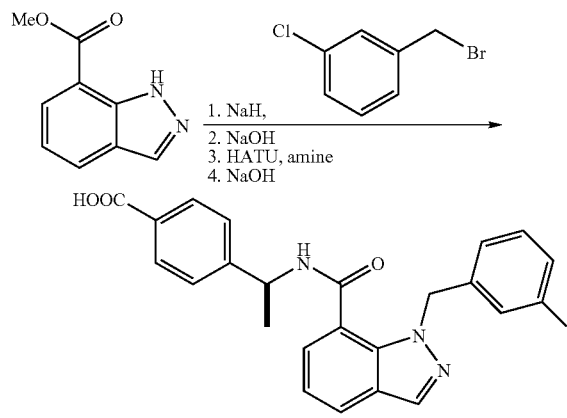

The remaining steps took place analogously as shown in Scheme 1 and described in Example 1 to yield the title compound.

$^1$H NMR (400 MHz, DMSO): δ 12.75 (bs, 1H), 9.75 (d, 1H), 8.90 (s, 1H), 8.1-7.9 (m, 4H), 7.55 (s, 1H), 7.45-7.3 (m, 5H), 7.35 (t, 1H), 5.80 (s, 2H), 5.335 (dq, 1H), 1.50 (d, 3H). MS-ESI (431.9).

Example 12

4-[(1S)-1-({[5-chloro-1-(3-chlorobenzyl)-1H-indazol-7-yl]carbonyl}amino)ethyl]benzoic acid

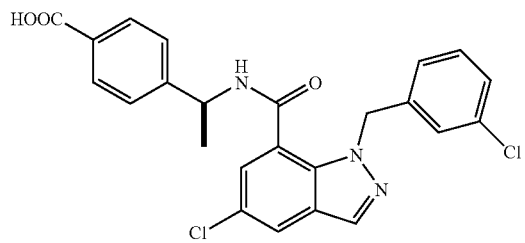

This example can be made in accordance with Example 11 starting with 2-amino-5-chloro-3-methylbenzoic acid.

$^1$H NMR (400 MHz, DMSO): δ 12.75 (bs, 1H), 9.50 (d, 1H), 8.80 (s, 1H), 8.20 (s, 1H), 7.9-7.7 (m, 3H), 7.60-7.3 (m, 6H), 5.70 (s, 2H), 5.35 (dq, 1H), 1.50 (d, 3H). MS-ESI (431.9).

Example 13

4-{(1S)-1-[({3-[(3-chlorophenyl)thio]-1H-indol-4-yl}carbonyl)amino]ethyl}benzoic acid

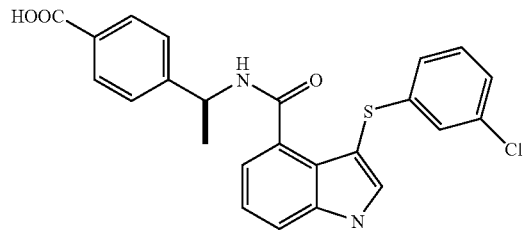

Step 1: methyl 3-[(3-chlorophenyl)thio]-1H-indole-4-carboxylate

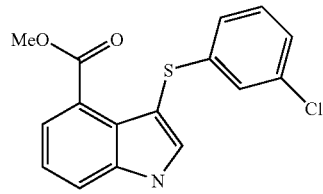

To a solution of commercially available methyl 1H-indole-4-carboxylate (300 mg, 1.71 mmol) in 5 mL DMF, at 0° C., was added 60% sodium hydride (137 mg, 3.42 mmol) and the resulting solution was stirred for 30 minutes. The disulfide (589 mg, 2.05 mmol) was added and the solution was stirred for 3 hours and then quenched with saturated aqueous ammonium chloride and the solution was extracted with ethyl acetate. The organic phases were then combined, washed with brine, dried over MgSO$_4$, filtered and concentrated in vacuo. The compound was purified by flash chromatography using column chromatography (5-50% EtOAc/hexanes) to yield 300 mg as a colorless oil. $^1$H NMR (500 MHz, CDCl3): δ 11.9 (bs, 1H), 8.3-8.1 (m, 2H), 7.9-7.5 (m, 6H), 4.0 (s, 3H).

Step 2: 4-{(1S)-1-[({3-[(3-chlorophenyl)thio]-1H-indol-4-yl}carbonyl)amino]ethyl}benzoic acid

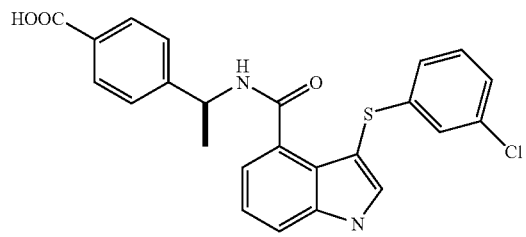

Hydrolysis, HATU coupling and hydrolysis on the ester took place analogously as shown in Scheme 1 and described in Example 1 to yield the title compound. $^1$H NMR (400 MHz, DMSO-d6): δ 12.3 (bs, 1H), 11.5 (bs, 1H), 8.1 (d, 1H), 7.5-7.0 (m, 6H), 6.9-6.30 (m, 6H), 4.7 (q, 1H), 0.9 (d, 3H).

Example 14

4-[(1S)-1-({[3-(3-chlorobenzyl)-1H-indol-4-yl]carbonyl}amino)ethyl]benzoic acid

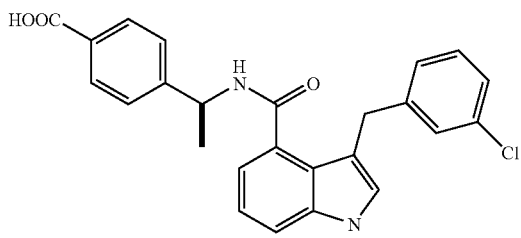

Step 1: methyl 3-(3-chlorobenzyl)-1H-indole-4-carboxylate

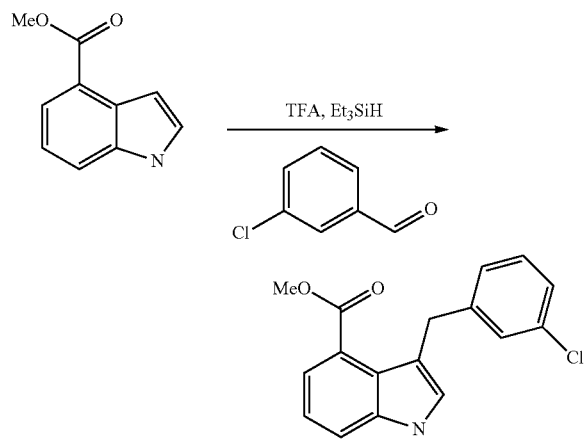

To a solution of commercially available methyl 1H-indole-4-carboxylate (5 g, 28.5 mmol) in 100 mL dichloromethane, at 0° C., was added 3-chlorobenzaldehyde (5 mL, 43.8 mmol), triethylsilane (15 mL, 93.9 mmol) and trifluoroacetic acid (5 mL, 64.9 mmol), and the resulting solution was stirred for ON as it warmed to rt. The reaction was then quenched with saturated aqueous sodium bicarbonate and the solution was extracted with dichloromethane. The organic phases were then combined, washed with brine, dried over MgSO$_4$, filtered and concentrated in vacuo. The resultant solid was washed with cold 10:1 hexanes:dichloromethane to yield 6 g of the title compound as a white solid. $^1$H NMR (500 MHz, d6-acetone): δ 8.5 (s, 1H), 8.0 (m, 2H), 7.4-7.1 (m, 5H), 5.7 (s, 2H), 4.0 (s, 3H).

Step 2: 4-[(1S)-1-({[3-(3-chlorobenzyl)-1H-indol-4-yl]carbonyl}amino)ethyl]benzoic acid

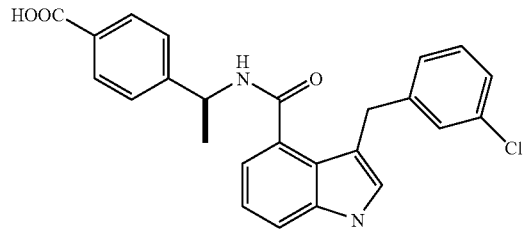

Hydrolysis, HATU coupling and hydrolysis on the ester took place analogously as shown in Scheme I to yield the title compound. $^1$H NMR (500 MHz, d6-acetone): δ 11.0 (bs, 1H), 10.3 (bs, 1H), 8.0 (d, 2H), 7.8 (m, 1H), 7.6 (d, 2H), 7.5 (d, 1H), 7.3-7.0 (m, 6H), 5.2 (dq, 1H), 4.4 (d, 1H), 4.1 (d, 1H), 1.6 (d, 2H). LRMS M−1 430.8 M+1 433.2.

Example 15

4-[(1S)-1-({[5-chloro-1-(3-chlorobenzyl)-1H-benzimidazol-7-yl]carbonyl}amino)ethyl]benzoic acid

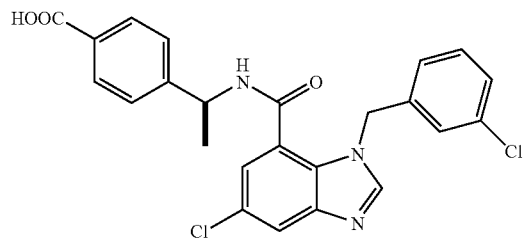

The title compound can be made as shown in Scheme 5. Hydrolysis, HATU coupling and hydrolysis on the ester took place analogously as described in Example 1 to yield the title compound. 1H NMR (500 MHz, d6-acetone): δ 11.0 (bs, 1H), 9.1 (d, 1H), 8.6 (s, 1H), 8.0 (m, 3H), 7.5-7.0 (m, 6H), 6.7 (d, 1H), 5.6 (AB q, 2H), 5.0 (dq, 1H), 1.4 (d, 3H). LRMS M−1 466.1 M+1 468.1.

Example 16

4-[(1S)-1-({[5-chloro-1-(3-chlorobenzyl)-1H-1,2,3-benzotriazol-7-yl]carbonyl}amino)ethyl]benzoic acid

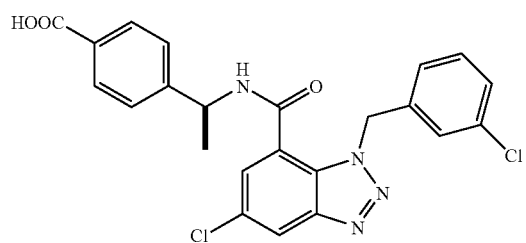

Step 1: Methyl 4-[(1S)-1-({5-chloro-2-[(3-chlorobenzyl)amino]-3-nitrobenzoyl}amino)ethyl]benzoate

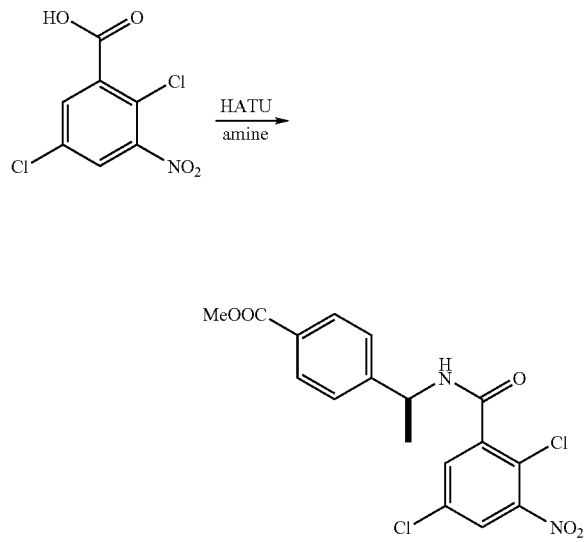

Methyl 4-{(1S)-1-[(2,5-dichloro-3-nitrobenzoyl)amino]ethyl}benzoate (500 mg, 1.26 mil) and 3-chlorobenzyl amine (1089 mg, 7.69 mmol) were dissolved in 50 ml THF. The mixture was refluxed overnight then cooled. The solvent was removed and the crude mixture purified by flash chromatography on silica gel. $^1$H NMR (400 MHz, DMSO): δ 9.25 (d, 1H), 8.20 (t, 1H), 8.15 (s, 1H), 7.95 (d, 2H), 7.70 (s, 1H), 7.60 (d, 2H), 7.30 (m, 2H), 7.15 (s, 1H), 7.05 (d, 1H), 5.10 (m, 2H), 4.10 (m, 2H), 4.85 (s, 3H), 1.45 (d, 3H).

Step 2: Methyl 4-[(1S)-1-({3-amino-5-chloro-2-[(3-chlorobenzyl)amino]benzoyl}amino)ethyl]benzoate Prepared from methyl 4-[(1s)-1-({5-chloro-2-[(3-chlorobenzyl)amino]-3-nitrobenzoyl}amino)ethyl]benzoate following procedure in Synlett. 1998, 1161. $^1$H NMR (400 MHz, DMSO): δ 8.90 (d, 1H), 7.95 (d, 2H), 7.45 (d, 2H), 7.30-7.20 (m, 3H), 7.05 (d, 1H), 5.25 (bs, 2H), 5.05 (m, 1H), 4.05-3.85 (m, 5H), 4.85 (s, 3H), 1.40 (d, 3H).

Step 3: Methyl 4-[(is)-1-({[5-chloro-1-(3-chlorobenzyl)-1h-1,2,3-benzotriazol-7-yl]carbonyl}amino)ethyl]benzoate Methyl 4-[(1S)-1-({3-amino-5-chloro-2-[(3-chlorobenzyl)amino]benzoyl}amino)ethyl]benzoate (169 mg, 0.358 mmol) was dissolved in 5 ml AcOH. Cool to 0° C. and add sodium nitrite (25.9 mg, 0.379 mmol) in 5 ml water over 1 hour. Stir RT overnight. Added an additional 0.5 eq sodium nitrite and stirred 1 hour. The mixture was poured into NaHCO$_3$ (sat.) and extracted with EtOAc. The organic layer was washed with brine and dried with MgSO$_4$. The solvent was removed and the crude mixture purified by flash chromatography on silica gel. $^1$H NMR (400 MHz, DMSO): δ 12.90 (bs, 1H), 9.35 (d, 1H), 8.50 (s, 1H), 7.90 (d, 2H), 7.80 (s, 1H), 7.60 (d, 2H), 7.30 (d, 1H), 7.20 (t, 1H), 7.05 (s, 1H), 6.85 (d, 1H), 6.05 (dd, 2H), 5.10 (m, 1H), 1.35 (d, 3H). MS-ESI (466.8).

Step 4: 4-[(1S)-1-({[5-chloro-1-(3-chlorobenzyl)-1H-1,2,3-benzotriazol-7-yl]carbonyl}amino)ethyl]benzoic acid

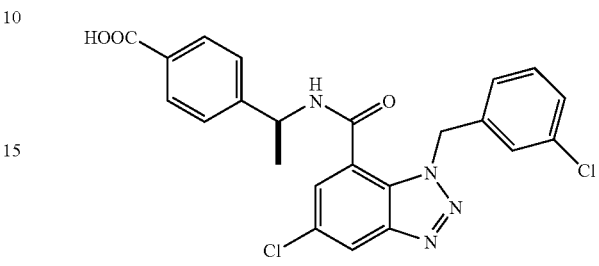

Hydrolysis of methyl 4-[(1S)-1-({[5-chloro-1-(3-chlorobenzyl)-1H-1,2,3-benzotriazol-7-yl]carbonyl}amino)ethyl]benzoate ester took place analogously as described in Example 1 to yield the title compound. $^1$H NMR (400 MHz, DMSO): δ 12.90 (bs, 1H), 9.35 (d, 1H), 8.50 (s, 1H), 7.90 (d, 2H), 7.80 (s, 1H), 7.60 (d, 2H), 7.30 (d, 1H), 7.20 (t, 1H), 7.05 (s, 1H), 6.85 (d, 1H), 6.05 (dd, 2H), 5.10 (m, 1H), 1.35 (d, 3H). MS-ESI (466.8).

What is claimed is:
1. A compound of Formula I

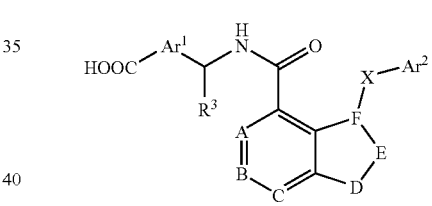

or a pharmaceutically acceptable salt thereof, wherein:
  each of A, B and C is independently selected from CH and C(R$^1$);
-D-E-F- is selected from the group consisting of:
  —C(R$^5$)═C(R)—N—,
  —C(R)═N—C(R)—,
  —C(R)═N—N—,
  —N═C(R)—N—,
  —N═N—N—,
  —C(R)$_2$—N═C—,
  —N(R)—C(R)═C—,
  —N(R)—N═C—,
  —O—N═C— and
  —S—N═C—
  wherein each R is independently selected from the group consisting of: hydrogen, C$_{1-4}$alkyl, C$_{1-4}$fluoroalkyl, C$_{1-4}$alkoxy, C$_{1-4}$fluoroalkoxy and acetyl;
  R$^5$ is selected from the group consisting of: hydrogen, halo, C$_{1-4}$alkyl, C$_{1-4}$fluoroalkyl, C$_{1-4}$-alkoxy, C$_{1-4}$-fluoroalkoxy and acetyl;
  X is a bond, —CH$_2$— or —CH$_2$—CH$_2$—, and X may additionally be —S—when -D-E-F- is —C(R$^5$)═N—C(R)—;
  Ar$^1$ and Ar$^2$ are independently selected from the group consisting of: C$_{3-6}$cycloalkyl, aryl, heteroaryl and heterocyclyl, or a fused analog of $C_{3-6}$cycloalkyl, aryl, heteroaryl and heterocyclyl, wherein $Ar^2$ is optionally substituted with one to three $R^2$ groups and $Ar^1$ is optionally substituted with one to three $R^4$ groups; and $R^1$, $R^2$, $R^3$ and $R^4$ are independently selected from the group consisting of: halo, $C_{1-4}$alkyl, $C_{1-4}$-fluoroalkyl, $C_{1-4}$alkoxy, $C_{1-4}$-fluoroalkoxy and acetyl.

2. The compound according to claim 1 wherein $R^3$ is methyl.

3. The compound according to claim 1 wherein $Ar^1$ is phenyl, optionally substituted with one to three $R^4$ groups.

4. The compound according to claim 1 wherein $Ar^2$ is phenyl, optionally substituted with one to three $R^2$ groups.

5. The compound according to claim 1 of Formula Ia

Ia

[Structure]

or a pharmaceutically acceptable salt thereof, wherein:
-D-E-F- is selected from the group consisting of:
—C($R^5$)=C(R)—N—,
—C(R)=N—N—,
—N(R)—C(R)=C—,
—N=C(R)—N— and
—N=N—N—,
wherein each R is independently selected from the group consisting of: hydrogen, $C_{1-4}$alkyl, $C_{1-4}$fluoroalkyl, $C_{1-4}$alkoxy, $C_{1-4}$fluoroalkoxy and acetyl;

$R^5$ is selected from the group consisting of: hydrogen, halo, $C_{1-4}$alkyl, $C_{1-4}$fluoroalkyl, $C_{1-4}$alkoxy, $C_{1-4}$fluoroalkoxy and acetyl;

X is a bond or —$CH_2$—; and $R^1$ and $R^2$ are independently selected from the group consisting of: halo, $C_{1-4}$alkyl, $C_{1-4}$fluoroalkyl, $C_{1-4}$alkoxy, $C_{1-4}$fluoroalkoxy and acetyl.

6. The compound according to claim 5 wherein X is —$CH_2$—.

7. The compound according to claim 5 wherein
each R is independently selected from the group consisting of: hydrogen, methyl, thrifluoromethyl, trifluoromethoxy and acetyl;

$R^5$ is selected from the group consisting of hydrogen, chloro, methyl, thrifluoromethyl, trifluoromethoxy and acetyl; and $R^1$ and $R^2$ are independently selected from the group consisting of: chloro, methyl, thrifluoromethyl, trifluoromethoxy and acetyl.

8. The compound according to claim 5 wherein -D-E-F- is —C($R^5$)=C(R)—N—.

9. The compound according to claim 5 wherein -D-E-F- is —C(R)=N—N—.

10. The compound according to claim 5 wherein -D-E-F- is: —N(R)—C(R)=C—.

11. The compound according to claim 5 wherein -D-E-F- is —N=C(R)—N—.

12. The compound according to claim 5 wherein -D-E-F- is —N=N—N—.

13. A compound according to claim 1 selected from the following:
(1) 4-{(1S)-1-[({1-[3-(trifluoromethyl)benzyl]-1H-indol-7-yl}carbonyl)amino]ethyl}benzoic acid;
(2) 4-[(1S)-1-({[1-(3-chlorobenzyl)-1H-indol-7-yl]carbonyl}amino)ethyl]benzoic acid;
(3) 4-{(1S)-1-[({1-[3-chloro-4-(trifluoromethoxy)benzyl]-1H-indol-7-yl}carbonyl)amino]ethyl}benzoic acid;
(4) 4-{(1S)-1-[({1-[2-(3-chlorophenyl)ethyl]-1H-indol-7-yl}carbonyl)amino]ethyl}benzoic acid;
(5) 4-[(1S)-1-({[1-(3-chlorobenzyl)-3-methyl-1H-indol-7-yl]carbonyl}amino)ethyl]benzoic acid;
(6) 4-[(1S)-1-({[3-chloro-1-(3-chlorobenzyl)-1H-indol-7-yl]carbonyl}amino)ethyl]benzoic acid;
(7) 4-[(1S)-1-({[3-acetyl-1-(3-chlorobenzyl)-1H-indol-7-yl]carbonyl}amino)ethyl]benzoic acid;
(8) 4-[(1S)-1-({[5-chloro-1-(3-chlorobenzyl)-1H-indol-7-yl]carbonyl}amino)ethyl]benzoic acid;
(9) 4-[(1S)-1-({[5-chloro-1-(3-chlorobenzyl)-1H-indol-7-yl]carbonyl}amino)ethyl]benzoic acid;
(10) 4-[(1S)-1-({[1-(3-chlorobenzyl)-2-methyl-1H-indol-7-yl]carbonyl}amino)ethyl]benzoic acid;
(11) 4-[(1S)-1-({[1-(3-chlorobenzyl)-1H-indazol-7-yl]carbonyl}amino)ethyl]benzoic acid;
4-[(1S)-1-({[5-chloro-1-(3-chlorobenzyl)-1H-indazol-7-yl]carbonyl}amino)ethyl]benzoic acid;
(12) 4-{(1S)-1-[({3-[(3-chlorophenyl)thio]-1H-indol-4-yl}carbonyl)amino]ethyl}benzoic acid;
(13) 4-[(1S)-1-({[3-(3-chlorobenzyl)-1H-indol-4-yl]carbonyl}amino)ethyl]benzoic acid;
(14) 4-[(1S)-1-({[5-chloro-1-(3-chlorobenzyl)-1H-benzimidazol-7-yl]carbonyl}amino)ethyl]benzoic acid; and
(15) 4-[(1S)-1-({[5-chloro-1-(3-chlorobenzyl)-1H-1,2,3-benzotriazol-7-yl]carbonyl}amino)ethyl]benzoic acid;
or a pharmaceutically acceptable salt of any of the aforementioned.

14. A pharmaceutical composition comprising a compound according to claim 1 in admixture with one or more physiologically acceptable carriers or excipients.

* * * * *